United States Patent [19]

Hoang et al.

[11] Patent Number: 5,629,006
[45] Date of Patent: May 13, 1997

[54] SKIN DISINFECTING FORMULATIONS

[75] Inventors: Minh Q. Hoang, Taylorsville; Mohammed A. Khan, Sandy; Anne M. Pazos, Salt Lake City; Scott D. Miles, Sandy, all of Utah

[73] Assignee: Becton, Dickinson and Company, Franklin Lakes, N.J.

[21] Appl. No.: 535,592

[22] Filed: Sep. 28, 1995

Related U.S. Application Data

[63] Continuation of Ser. No. 266,823, Jun. 27, 1994, abandoned.

[51] Int. Cl.$^6$ ............................. A01N 25/00; A01N 25/02
[52] U.S. Cl. ............................. 424/405; 422/1; 422/8; 510/157; 510/158
[58] Field of Search .................... 424/401, 405; 422/1, 28; 252/106

[56] References Cited

U.S. PATENT DOCUMENTS

| | | | |
|---|---|---|---|
| 4,336,151 | 6/1982 | Like | 252/106 |
| 4,769,169 | 9/1988 | Lomax | 252/106 |
| 4,836,986 | 6/1989 | Ogunbiyi | 422/28 |
| 4,941,989 | 7/1990 | Kramer | 252/102 |
| 5,015,228 | 5/1991 | Columbus | 604/51 |
| 5,047,249 | 9/1991 | Rothman | 424/543 |
| 5,073,371 | 12/1991 | Turner | 424/401 |
| 5,266,598 | 11/1993 | Ninomiya | 514/635 |
| 5,298,222 | 3/1994 | O'Leary | 422/28 |
| 5,336,497 | 8/1994 | Guerrero | 424/401 |

OTHER PUBLICATIONS

Elaine L. Larson, PhD; Arlene M. Butz, ScD; Donna L. Gullette, MSN; Barbara A. Laughton, PhD, "Alcohol for Surgical Scrubbing?" *Infect Control Hosp. Epidemiol*, 1990/vol. 11, No. 3. pp. 139–143.

Allan J. Morrison, Jr., MD; Jean Gratz, BS, MT (ASCP); Ignacio Cabuezdo, MD; Richard P. Wenzel, MD, "The Efficacy of Several New Hdnwashing Agents for Removing Non–Transient Bacterial Flora from Hands," *Infection Control*, 1986/vol. 7, No. 5., pp. 268–272.

Arlene M. Butz, RN, ScD; Barbara E. Laughton, PhD; Donna L. Gullette, RN, MSN; Elaine L. Larson, RN; PhD. "Alcohol–impregnated Wipes as an Alternative in Hand Hygiene," *American Journal of Infection Control*. vol. 18, No. 2, Apr. 1990, pp. 70–76.

*Primary Examiner*—Gollamuei S. Kishore
*Attorney, Agent, or Firm*—Bruce S. Wientraub; Nanette S. Thomas

[57] ABSTRACT

A skin disinfecting formulation for use as a skin washing agent, comprising an alcohol, a block copolymer, a foaming surfactant, an emulsifier, a cleaning agent, a polyalkylene glycol, an emollient and water. The skin disinfecting formulation will not irritate the skin and will provide antimicrobial effectiveness to the skin.

7 Claims, No Drawings

SKIN DISINFECTING FORMULATIONS

This application is a continuation of application Ser. No. 08/266,823, filed Jun. 27, 1994 now abandoned.

BACKGROUND OF THE INVENTION

1. Field of the Invention

This invention relates to skin disinfecting formulations for providing antimicrobial effectiveness to the skin without irritation or dryness. The skin disinfecting formulations comprising alcohol are particularly useful in the healthcare profession.

2. Description of Related Art

Handwashing by healthcare professionals is an essential component of infection control activities. Healthcare professionals attending to patient care wash their hands to control the spread of infection from patient to patient and surgical procedures are routinely proceeded by surgical hand scrubbing and patient pre-operative skin prepping.

Hand washing procedures are performed in several ways. Several procedures include an ordinary antimicrobial bar soap, a skin disinfecting or preoperative prepping agent or robbing alcohol. The use of these procedures repeatedly is hard and rough on hands.

Commercially available scrubs include detergents and an antimicrobial agent or a preservative. Such antimicrobial or preservative agents include iodine formulations, iodophors, phenolic compounds such as parachlorometaxylenol and hexachlorophene and bis-biguandies such as chlorhexidine gluconate.

Although alcohol in general is recognized for its very effective disinfecting properties, it is not used directly with skin or in scrub formulations because it is a defatting agent. When alcohol is applied to the human skin, it makes it very dry, often developing chapped and cracked skin. Furthermore, it is difficult to formulate a detergent solution with alcohol that will foam like ordinary soaps and detergents when used with water.

However, due to the disinfecting properties of alcohol, it is desirable to produce a skin disinfecting formulation with alcohol which is mild and gentle to the skin, foams and is effective against microorganisms.

SUMMARY OF THE INVENTION

The present invention is a skin disinfecting formulation that provides antimicrobial effectiveness and is mild and gentle to human skin. The skin disinfecting formulation desirably comprises an alcohol, a block copolymer, a foaming surfactant, an emulsifier, a cleaning agent, a polyalkylene glycol, a moisturizer and/or emollient and water.

Preferably, the skin disinfecting formulation may further comprise a thickening agent or a preservative.

Most preferably, the skin disinfecting formulations comprise by weight:

(a) from about 50% to about 80% of an alcohol;
(b) from about 0.02% to about 5% of a block copolymer;
(c) from about 5% to about 25% of a foaming surfactant;
(d) from about 0% to about 3% of a thickening agent;
(e) from about 1% to about 5% of an emulsifier;
(f) from about 0% to about 5% of a preservative;
(g) from about 1% to about 10% of a cleaning agent;
(h) from about 0.5% to about 5% of a polyalkylene glycol;
(i) from about 0.05% to about 5% of a moisturizer and/or emollient; and
(j) from about 6% to about 30% of water.

The skin disinfecting formulations of the present invention are useful in providing substantial antimicrobial effectiveness and surprisingly, provide substantial non-irritancy to the skin in view of the alcohol component of the formulations.

Another attribute of the skin disinfecting formulations is its ability to not dry the skin.

A most significant advantage of the skin disinfecting formulations is its use in the health care profession.

Further advantages of the skin disinfecting formulations of the present invention is its significant foaming properties, good solubility in water and adequate detergency.

The skin disinfecting formulations of the present invention will disinfect the skin while also providing emolliency to the skin. Further, the skin disinfecting formulations of the present invention can also be used as a general purpose hand wash to decontaminate the hands of healthcare professionals before examining any patient.

Healthcare professionals perform a routine hand scrubbing procedure many times a day. The typical and/or commonly used scrub solutions contain chemical compounds such as iodine, chlorhexidine gluconate, PCMX and hexachlorophene. All of these chemical compounds disinfect the skin as well as bind to the skin, thus providing persistent activity. Since healthcare professionals scrub many times a day, the chemical compounds build-up on the skin and the healthcare professional will leave work with accumulated chemical compounds on their hands. Therefore, the skin disinfecting formulations of the present invention are excellent solvents for these accumulated chemical compounds to be washed off the skin and at the same time, disinfect the hands by killing the microorganisms and viruses. Therefore, the skin disinfecting formulations of the present invention may be used by healthcare professionals to wash their hands before leaving the work place. This would be the "final" wash.

Surprisingly, the formulations of the present invention provide substantially effective skin disinfecting properties with the use of alcohol in the formulations as well as being mild and gentle to the skin, having substantially excellent foaming properties and substantially effective against microorganisms.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The skin disinfecting formulations of the present invention comprise an alcohol, a block copolymer, a foaming surfactant, an emulsifier, a preservative, a cleaning agent, a polyalkylene glycol, a moisturizer and/or emollient and water. The skin disinfecting formulations may further comprise a thickening agent.

An alcohol is preferably used in the skin disinfecting formulations because of its bactericidal properties. Generally, a concentration of alcohol over 50% is an effective germicidal agent. It kills gram-positive, gram-negative bacteria fungi; and many viruses. The potent activity of alcohol against micro-organisms is due to its denaturation of proteins and enzymes and dehydration.

An alcohol for use in the skin disinfecting formulation includes, but is not limited to, isopropyl alcohol, ethanol and methyl alcohol.

The preferred alcohol for use in the skin disinfecting formulations is isopropanol and ethanol. Preferably, isopropyl alcohol may be present in the skin disinfecting formulation in an amount from about 50 to about 80 weight percent, and most preferably at about 70 weight percent.

Most preferably, the block copolymer of the present invention is polydimethyl siloxane-polyethylene oxide (PDMS/PEO). PDMS/PEO is commercially available as SILWET® surfactant (trademark of Union Carbide, 39 Old Ridgebury Road, Danbury, Conn. 06817-0001) sold by Union Carbide.

SILWET surfactants are chemically unique and should not be confused with conventional polydimethylsiloxanes because they are composed of a siloxane backbone with organic polyalkyleneoxide pendants, forming chemical structures whose variations provide a wide range of useful performance characteristics. SILWET surfactants are a class of polyalkyleneoxide dimethylsiloxane copolymers.

SILWET surfactants are nonionic, concentrated, and function in aqueous and non-aqueous systems. SILWET surfactants comprise the following features: low surface tension; high wetting; good dispersing, emulsifying, lubricity; sheen, gloss enhancing; static suppressing; contribute to antifoaming; moderate profoaming; broad range of solubility and aqueous cloud points; low volatility, good thermal stability; compatible with organic surfactants and system components, and low toxicity.

SILWET surfactants are polyalkylene oxide-modified polydimethylsiloxanes. These block copolymers are of two distinct structural types. The major class is a linear polydimethysiloxane to which polyethers have been grained through a hydrosilation reaction. This process results in an alkyl-pendant (AP type) copolymer, in which the polyalkylene oxide groups are attached along the siloxane backbone through a series of hydrolytically stable Si—C bonds. They have the following general formula:

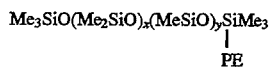

where PE=—CH$_2$CH$_2$CH$_2$O(EO)$_m$(PO)$_n$Z

In this formula, Me represents methyl, EO represents ethyleneoxy, PO represents 1,2-propyleneoxy, and Z can be either hydrogen or a lower alkyl radical.

The other class is a branched polydimethylsiloxane to which polyesters have been attached through condensation chemistry. This creates an alkoxy-end -blocked (AEB Type) copolymer, in which the polyalkylene oxide groups are attached at the ends of the silicone backbone through Si—O—C bonds. This linkage offers limited resistance to hydrolysis under neutral or slightly alkaline conditions, but breaks down quickly in acidic environments. They have the general formula:

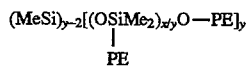

where PE=—(EO)$_m$(PO)$_n$R and R represents a lower alkyl group.

By varying the coefficients x, y, m, and n, a broad range of SILWET surfactants are produced. These surfactants offer unique properties and performance that are not readily achievable with conventional organic surfactants.

Preferably, a SILWET surfactant may be present in the skin disinfecting formulations in an amount from about 0.02 to about 5 by weight percent and most preferably at about 0.25 weight percent.

A foaming surfactant is preferably used in the skin disinfecting formulations because the foaming surfactant enhances the foamability of the formulation. Desirable foaming surfactants for the skin disinfecting formulations include, but are not limited to, ammonium fatty sulfo succinate, cocamide dea, alkonolamides such as cocodiethanolamide, amine oxides such as cetyldimethyl amino oxide and amphoterics such as isostearoamphoropionate and laura midopropyl betaine surfactant. Such foaming surfactants are very mild with respect to skin irritation.

A suitable foaming surfactant for the skin disinfecting formulations is an ammonium lauryl sulfosuccinate, commercially available as MONAMATE® LNT-40 (a trademark of MONA Industries, Paterson, N.J.) sold by MONA.

Another suitable foaming surfactant for the skin disinfecting formulations is a fatty acid alkanolamide, commercially available as MONAMID® ISA-35 (a trademark of MONA Industries, Paterson, N.J.) sold by MONA.

Another suitable foam builder for the skin disinfecting formulations is an amphoteric surfactant, commercially available as MONATERIC surfactant (a trademark of MONA Industries, Paterson, N.J.) sold by MONA.

Another suitable foaming surfactant for the skin disinfecting formulations is a lauramidorpropyl betaine, commercially available as MONATERIC® LMAB (a trademark of MONA Industries, Paterson, N.J.) sold by MONA.

Preferably, the foaming surfactant is present in the skin disinfecting formulations in an amount from about 5 to about 25 weight percent and most preferably at about 17 weight percent.

A thickening agent may be used in the skin disinfecting formulations to adjust the viscosity and stability of the formulations. Most importantly, the thickening agent must be soluble in about 70% alcohol.

A desirable thickener originates from cellulosic materials such as starch, methocel (methyl cellulose ethers) and hydroxyethyl cellulose. Other thickeners include high molecular weight pluronic surfactants and acrylic such as carbopol polymers.

It is believed that a more hydrophobic thickener provides a cellar composition and improves activity of the composition because it uses a minimum amount of water from the composition to provide the thickening activity. A less hydrophilic thickener may cause the skin disinfecting formulations to be turbid or milky because the skin disinfecting formulations may precipitate if there is not sufficient water in the composition.

A suitable thickening agent for the skin disinfecting formulations is a hydroxypropyl methylcellulose, METHOCEL® 40-100 (a trademark of the Dow Chemical Company, Midland, Mich.) sold by The Dow Chemical Company. METHOCEL® thickener is 91% hydroxypropyl methylcellulose which dissolves in water, is nonionic and is a highly efficient water retention agent.

Another suitable thickening agent is a nonionic surfactant, block copolymer that is generically classified as poly (oxypropylene) poly-(oxyethylene) condensate and is commercially available as PLURONIC® polyol (trademark of BASF, Wyandotte Corp., Wyandotte, Mich.). A particular PLURONIC polyol that is useful in the skin disinfecting formulations of the present invention includes, but is not limited to F127.

Preferably, the thickening agent may be present in the skin disinfecting formulations in an amount from about 0 to about 3 weight percent and most preferably at about 1 weight percent.

An emulsifier is used in the skin disinfecting formulations to disperse oily emollients in water solution. Most important, an emulsifier is a solubilizer.

A suitable emulsifier for the skin disinfecting formulations is an ethoxylated (75 moles) lanolin, Solulan® 75 (trademark of Amerchol Corporation, Edison, N.J.) sold by Amerchol Corporation (CTFA adopted name is PEG-75 lanolin).

Preferably, an emulsifier is present in the skin disinfecting formulations in an amount from about 1 to about 5 weight percent and most preferably at about 3 weight percent.

Alcohol is an excellent antimicrobial agent and will preserve the skin disinfecting formulation very well. However, when the formulation is applied to the skin, the alcohol will evaporate after a period of time. Thus, a small amount of a preservative may be added to the skin disinfecting formulation to preserve the antimicrobial effect of the formulation for an extended period of time.

The preservative is selected so as not to upset desirable physical and chemical properties of human skin. A properly selected preservative maintains stability under use and storage conditions (pH, temperature, light, etc.), for a required length of time. It will also prevent the growth of microbes and/or is effective in killing microbes to achieve a continuing antimicrobial effect.

A suitable preservative may be selected from the class of phenolics such as parachlorometaxylenol, hexetidine or bisbiguanides such as chlorhexidine gluconate. Most preferably, the preservative is parachlorometaxylenol.

Preferably, the preservative may be present in the skin disinfecting formulations in an amount from about 0 to about 5 weight percent and most preferably at about 0.5 weight percent.

A cleaning agent is used in the skin disinfecting formulations as a detergent to deep clean the hands. Most importantly, a cleaning agent is a surface active agent with good detergency.

A suitable cleaning agent for the skin disinfecting formulations is ethoxylated linear fatty alcohols or a nonylphenoxypoly (ethyleneoxy) ethanol surfactant, commercially available as IGEPAL® CO-720 surfactant (a trademark of GAF Corporation, 1361 Alps Road, Wayne, N.J. 07470) sold by GAF Chemicals Corporation. IGEPAL surfactant is nonionic in nature and has excellent cleaning and foaming properties.

Preferably, the cleaning agent is present in the skin disinfecting formulations in an mount from about 1 to about I 0 weight percent and most preferably at about 8 weight percent.

A polyalkylene glycol is used in the skin disinfecting formulations to serve as a skin oil substitute. A polyalkylene glycol is a synthetic oily substance and is typically characterized as a skin conditioner. The selection of a polyalkylene glycol is based on its biocompatibility and its ability to protect the skin from drying and chapping.

A preferable polyalkylene glycol in the skin disinfecting formulations is talloweth, 60 myristalglycol, commercially available as ELFACOS® GT282S (trademark of Akzo Chemic America, Chicago, Ill.) sold by Organic Chemicals.

Preferably, the polyalkylene glycol is present in the skin disinfecting formulations in an amount from about 0.5 to about 5 weight percent and most preferably at about 3 weight percent.

To counter the drying of skin by the presence of alcohol in the skin disinfecting formulations, a moisturizer and/or emollient is included.

Emollients in their physical form are thin liquids, oils of various viscosities, fatty solids or waxes. Hydrocarbons function essentially as emollients by virtue of their ability to lubricate and/or hold water at the skin surface due to their relative occlusivity. Mineral oil is such a fluid. Some emollients are hydrophilic (glycerin, propylene glycol) and are water soluble lubricants and humectants. Since emollients may be fatty chemicals, oily or waxy in nature, they can impart barrier properties to formulations and are then referred to as moisturizers.

Moisturizers are substances which provide external lubricant behavior, such as to soften and soothe the skin because they encourage skin water retention.

The function of the moisturizer and/or emollient in the skin disinfecting formulations is to provide relief for dry and sensitive skin. Therefore, chapping of the skin may be prevented. In addition, the moisturizer and/or emollient does not leave a tacky after feel on the skin.

Suitable moisturizers and/or emollients in the skin disinfecting formulations includes lanolin, derivatives of lanolin such as the ethoxylated acetylated alcohol and surface active alcohol derivatives of lanolin, propylene glycol, polypropylene glycol, polyethylene glycol, lanolin and lanolin derivatives, mineral oils, fatty alcohols and glycerin.

A suitable moisturizer and/or emollient is selected from lanolin derivatives, polyols and cetylethers. Most preferably, the moisturizer and/or emollient in the skin disinfecting formulations is propylene cetylether.

Preferably, moisturizers and/or emollients are present in the skin disinfecting formulations in an amount from about 0.05 to about 5 weight percent and most preferably at about 0.2 weight percent.

Adjustment of the pH of the skin disinfecting formulation is desirable so that it is compatible with the pH of the skin and to avoid unnecessary irritation to the skin. Small amounts, less than about 1.0% of a nontoxic acidic substance may be added to the skin disinfecting formulations.

Suitable acids include hydrochloric acid, sulfuric acid, phosphoric acid, citric acid, lactic acid and gluconic acid.

The skin disinfecting formulations may be adjusted to a pH within the range from about 5 to about 8. Most preferably, the pH is within the range of about 6.5 to about 7.5.

Other ingredients which are conventional or desirable for aesthetic purposes may also be added to the skin disinfecting formulations as long as they do not adversely affect the overall properties of the formulation. Such ingredients may include polyvinyl pyrrolidone, commercially available as KOLLIDON® (tradename of BASF Wyandotte Corporation, Parsippany, N.J. 07054) sold by BASF.

If desired, the skin disinfecting formulations of the invention may include a perfume or fragrance to provide a pleasing scent or a dye to provide a characteristic color.

The skin disinfecting formulations of the present invention are prepared by first mixing the alcohol and water. Then the thickening agent is dispersed in the alcohol and water mixture. A small amount of sodium hydroxide is added to hydrate the cellulose. The mixture is agitated until the thickening agent is fully dissolved and no granulation remains. The remaining ingredients are then added and mixed until a clear homogeneous liquid solution is obtained.

Generally, the skin disinfecting formulations may be in liquid form but may also be in the form of a gel or ointment.

The following examples are not limited to any specific embodiment of the invention, but are only exemplary.

EXAMPLE 1

PREPARATION OF SKIN DISINFECTING FORMULATIONS

The skin disinfecting formulations of the present invention were prepared with the ingredients as shown in Tables 1 and 2.

In a mixing vessel, isopropyl alcohol and water were first mixed together. Then the remaining selected ingredients were mixed in. In some formulations a thickening agent was mixed in with the alcohol and water until the thickening agent was dispersed. A small amount of sodium hydroxide was then added to hydrate the cellulose. The mixture was then agitated until all the thickening agent was dissolved and no granulation remained. The remainder of the ingredients were added in given order with sufficient stirring to obtain a clear homogenous solution. A sufficient amount of 6N hydrochloric acid was then added if needed to adjust the pH to 6.0–8.0.

TABLE 1

| Ingredients | 341-E | 341-EE | 341-EEA | 341-EEB | 341-EEC | 341-E1 |
|---|---|---|---|---|---|---|
| Alcohol: | | | | | | |
| Isopropyl Alcohol | 70.00 | — | — | — | 70.00 | 70.00 |
| Ethanol SD-40 | — | 60.00 | 60.00 | 60.00 | — | — |
| Block Copolymer: | | | | | | |
| Silwet L-7200 | — | — | 0.20 | 0.25 | 0.25 | — |
| Foaming Surfactant: | | | | | | |
| Monateric ISA-35 | 10.00 | 10.00 | 10.00 | 10.00 | 10.00 | 10.00 |
| Monamid 150ADD | 7.00 | 7.00 | 7.00 | 7.00 | 7.00 | 7.00 |
| Monamate LNT-40 | — | — | — | — | — | — |
| Monateric LMAB | — | — | — | — | — | — |
| Thickening Agent: | | | | | | |
| Pluronic F-127 | — | — | — | — | — | — |
| Methocel 40-100 | 0.60 | 1.50 | 1.00 | 1.00 | 1.00 | 1.00 |
| Emulsifier: | | | | | | |
| PEG-75 Lanolin | 3.00 | 3.00 | 3.00 | 3.00 | 3.00 | 3.00 |
| Preservative: | | | | | | |
| Chlorhexidine Gluconate (20%) | — | — | — | — | — | 2.50 |
| Hexetidine | — | — | — | — | — | — |
| PCMX | — | 0.50 | 0.50 | 0.50 | 0.5 | — |
| Polyalkylene Glycol: | | | | | | |
| ELFACOS GT2825 | — | — | — | — | — | — |
| Cleaning Agent: | | | | | | |
| Igepal CO-720 | — | — | — | — | — | — |
| Moisturizer and/or Emollient: | | | | | | |
| HO Emollient | — | — | 0.20 | 0.05 | 0.05 | — |
| Other: | | | | | | |
| Fragrance | — | 0.08 | 0.08 | 0.08 | 0.08 | — |
| EDTA | — | 0.05 | 0.05 | 0.05 | 0.05 | — |
| PVP-K90 | — | — | — | — | — | — |
| Water Deionized | 9.40 | 17.87 | 17.97 | 18.07 | 8.07 | 6.5 |
| | 100 | 100 | 100 | 100 | 100 | 100 |

TABLE 2

| Ingredients | 341-E2 | 341-B1 | 341-C | 341-F | 341-F1 | 341-F2 |
|---|---|---|---|---|---|---|
| Alcohol: | | | | | | |
| Isopropyl Alcohol | 70.00 | 70.00 | 70.00 | — | 70.00 | — |
| Ethanol SD-40 | — | — | — | 60.00 | — | 60.00 |
| Block Copolymer: | | | | | | |
| Silwet L-7200 | — | — | — | — | — | — |
| Foaming Surfactant: | | | | | | |
| Monateric ISA-35 | 10.00 | — | 10.00 | — | 10.00 | — |
| Monamid 150ADD | 7.00 | — | 5.00 | 8.00 | 7.00 | 8.00 |

TABLE 2-continued

| Ingredients | 341-E2 | 341-B1 | 341-C | 341-F | 341-F1 | 341-F2 |
|---|---|---|---|---|---|---|
| Monamate LNT-40 | — | 1.00 | — | — | — | — |
| Monateric LMAB | — | 15.40 | — | — | — | — |
| Thickening Agent: | | | | | | |
| Pluronic F-127 | — | — | — | — | 5.00 | — |
| Methocel 40-100 | 0.60 | 0.60 | — | 0.60 | — | 0.60 |
| Emulsifier: | | | | | | |
| PEG-75 Lanolin | 3.00 | 3.00 | 3.00 | 4.00 | 2.00 | 4.00 |
| Preservative: | | | | | | |
| Chlorhexidine Gluconate (20%) | — | — | — | — | — | 2.50 |
| Hexetidine | 1.00 | — | — | — | — | — |
| PCMX | — | — | — | — | — | — |
| Polyalkylene Glycol: | | | | | | |
| ELFACOS GT2825 | — | — | 3.00 | — | 5.00 | — |
| Cleaning Agent: | | | | | | |
| Igepal CO-720 | — | — | — | 8.00 | — | 8.00 |
| Moisturizer and/or Emollient: | | | | | | |
| HO Emollient | — | — | — | — | — | — |
| Other: | | | | | | |
| Fragrance | — | — | — | — | — | — |
| EDTA | — | 0.10 | — | — | — | — |
| PVP-K90 | — | — | 2.00 | — | 1.00 | — |
| Water Deionized | 8.40 | 9.90 | 7.00 | 19.40 | — | 16.90 |
| | 100 | 100 | 100 | 100 | 100 | 100 |

EXAMPLE 2

BACTERICIDAL EFFECTIVENESS EVALUATION

The formulations from EXAMPLE 1 were evaluated for bactericidal characteristics against target micro-organisms, namely Staphylococcus Aureus, Pseudomonas Aeruginosa, Candida Albicans and Escherichia Coli. These are the standard micro-organisms representing gram positives, gram negatives and fungus classifications. The bactericidal effectiveness testing procedure was conducted as follows:

5 ml of the formulation was added to a sterile tube. A microbial challenge of 0.1 ml containing the target micro-organism with appropriate count was added to the 5 ml test solution. At exposure times of 1 and 5 minutes, a 1.0 ml sample was transferred to 9.0 ml of Difco Dey Engley neutralizing broth. Subsequent 1.0 ml samples were transferred to Difco Dey Engley neutralizing broth base. The procedure was performed at full strength and at dilutions of 1:10, 1:100 and 1:1000. All samples were incubated at 30°–35° C. for 48 hours.

Nutrient agar pour plates were prepared from each sample and examined for the presence of colonies after a minimum of 48 hours.

The results of the effectiveness testing is given below in TABLE 3 that follow.

The data indicates that all formulations tested have excellent antimicrobial effectiveness at full strength. When the formulations were diluted 1:10, the formulations, in general lost the antimicrobial properties. All other dilutions had no antimicrobial effectiveness. The data confirms that the activity of alcohol below 50% is not acceptable.

Since the skin disinfecting formulation is intended to be used undiluted, the killing power of the undiluted solution was the most important factor considered. However, testing was conducted at several dilutions to assess the bactericidal power of the solution.

TABLE 3

| | BACTERICIDAL EFFICACY OF FORMULATIONS (Kill Time in Minutes) | | | | | | | | |
|---|---|---|---|---|---|---|---|---|---|
| Organism | Dilutions | 341-EE | 341-E1 | 341-E2 | 341-B1 | 341-C | 341-F | 341-F1 | 341-F2 |
| *Staphylococcus aureus* | FS | 1 | 1 | 1 | 1 | 1 | 1 | 1 | 1 |
| Challenge: 1.00E + 07 | 1:10 | Pos | Pos | Pos | Pos | Pos | Pos | Pos | Pos |
| | 1:100 | Pos | Pos | Pos | Pos | Pos | Pos | Pos | Pos |
| *Pseudomonas aeurginosa* | FS | 1 | — | — | 1 | 1 | 1 | 1 | — |
| Challenge: 1.00E + 0.7 | 1:00 | Pos | — | — | 5 | Pos | Pos | Pos | — |
| | 1:100 | Pos | — | — | Pos | Pos | Pos | Pos | — |
| *Candida albicans* | FS | 1 | — | — | — | — | — | 1 | — |
| Challenge: 1.00E + 0.6 | 1:10 | Pos | — | — | — | — | — | 1 | — |

TABLE 3-continued

BACTERICIDAL EFFICACY OF FORMULATIONS
(Kill Time in Minutes)

| Organism | Dilutions | 341-EE | 341-E1 | 341-E2 | 341-B1 | 341-C | 341-F | 341-F1 | 341-F2 |
|---|---|---|---|---|---|---|---|---|---|
| Escherichia coli | 1:100 | Pos | — | — | — | — | — | Pos | — |
| Challenge: 5.00E + 08 | FS | 1 | — | — | 1 | — | — | 1 | — |
|  | 1:10 | Pos | — | — | Pos | — | — | Pos | — |
|  | 1:100 | Pos | — | — | Pos | — | — | Pos | — |

Note:
FS = Full Strength
Pos = Not killed in 5 minutes

EXAMPLE 3

BIO COMPATIBILITY EVALUATION

Formulations 341-E and 341-C from EXAMPLE 1 were tested for primary skin irritation. Healthy, female New Zealand albino rabbits were individually housed and identified by an ear tag. The animals' backs were clipped free of fur. Two sites were chosen on each rabbit, with the skin left intact on one site and the skin abraded on the other site. 0.5 ml of each formulation was applied to each test site, covered with gauze, and covered with a non-reactive tape. The rabbits were then wrapped with a binder. After 24 hours, the tape and binder were removed and an evaluation of the skin for erythema and edema was performed. A subsequent evaluation was performed 72 hours post application. The results are reported in Table 4.

TABLE 4

| | | DERMAL REACTION | | | |
|---|---|---|---|---|---|
| | | 24 HOURS | | 72 HOURS | |
| RABBIT TAG NO. | REACTION | ABRADED | INTACT | ABRADED | INTACT |
| 4790 | ERYTHEMA | 0 | 0 | 0 | 0 |
|  | EDEMA | 0 | 0 | 0 | 0 |
| 4782 | ERYTHEMA | 0 | 0 | 0 | 0 |
|  | EDEMA | 0 | 0 | 0 | 0 |
| 4792 | ERYTHEMA | 0 | 0 | 0 | 0 |
|  | EDEMA | 0 | 0 | 0 | 0 |
| 4793 | ERYTHEMA | 0 | 0 | 0 | 0 |
|  | EDEMA | 0 | 0 | 0 | 0 |
| 4783 | ERYTHEMA | 0 | 0 | 0 | 0 |
|  | EDEMA | 0 | 0 | 0 | 0 |
| 4780 | ERYTHEMA | 0 | 0 | 0 | 0 |
|  | EDEMA | 0 | 0 | 0 | 0 |

EVALUATION OF SKIN REACTION:

| ERYTHEMA AND ESCHAR FORMATION: | VALUE | EDEMA FORMATION: | VALUE |
|---|---|---|---|
| No erythema | 0 | No edema | 0 |
| Very slight erythema (barely perceptible) | 1 | Very slight edema (barely perceptible) | 1 |
| Well-defined erythema | 2 | Slight edema (edges of area well defined by definite raising) | 2 |
| Moderate to severe erythema | 3 | Moderate edema (raised approx. 1 mm) | 3 |
| Severe erythema | 4 | Severe edema | 4 |
| (beet redness to slight eschar formation injuries in depth) | | (raised more than 1 mm and extending beyond the area of exposure) | |

| DATA ANALYSIS: | |
|---|---|
| INDEX* | EVALUATION |
| 0.00 | No irritation |
| 0.01–0.99 | Irritation barely perceptible |
| 1.00–1.99 | Slight irritation |
| 2.00–2.99 | Mild irritation |
| 3.0–5.99 | Moderate irritation |
| 6.00–8.00 | Severe irritation |

$$* \frac{\text{Total of 48 individual scores for erythema and edema}}{24} = \text{Primary Irritation Index}$$

$0/24 = 0$

Both formulations showed an irritation index of 0 on a rating system 0–8 whereby 0 is non-irritant and 8 is severed irritant to the rabbit skin.

EXAMPLE 4

STABILITY EVALUATION

Formulation 341-E from EXAMPLE 1 was tested for stability of the formulation with respect to the active ingredient which is the concentration of alcohol. 22 mls of the formulation was packaged in E-Z Scrub® packages (a trademark of Becton Dickinson and Company, 1 Becton Drive, Franklin Lakes, N.J.). The packages were aged at room temperature and 37° C. respectively, for five months.

The data indicates that the formulation is stable under the conditions tested. The concentration of alcohol is within 10% of the label claim.

Table 5 reports the data from the % alcohol assay. The assay was made by using gas chromatograph method which is a standard technique known to persons skilled in the art.

TABLE 5

| Sample I.D. | Mo. 0 | Mo. 1 | Mo. 2 | Mo. 3 | Mo. 4 | Mo. 5 |
|---|---|---|---|---|---|---|
| % Alcohol-Room Temperature | | | | | | |
| 9 mil | 67.0 | 68.8 | 69.6 | * | 71.7 | 70.6 |
| 12 mil | 66.3 | 68.0 | 68.8 | * | 69.8 | 68.0 |
| % Alcohol-37° C. | | | | | | |
| 9 mil | 67.0 | 69.9 | 70.5 | 69.6 | 67.2 | 68.3 |
| 12 mil | 66.3 | 68.4 | 69.5 | 69.7 | 69.0 | 68.2 |

*Data not available

What is claimed is:

1. A skin disinfecting formulation comprising:
   (a) an alcohol in an amount from about 50 to about 80 weight percent of the total composition;
   (b) a polyalkylaneoxide dimethylsiloxane copolymer in an amount from about 0.02 to about 5 weight percent of the total composition;
   (c) a lauramidorpropyl betaine, a fatty acid alkanolamide, an ammonium lauryl sulfosuccinate, or an amphoteric surfactant in an amount from about 5 to about 25 weight percent of the total composition;
   (d) ethoxylated lanolin in an amount from about 1 to about 5 weight percent;
   (e) nonylphenoxy polyethylenoxy alcohol or ethoxylated linear fatty alcohols in an amount from about 1 to about 10 weight percent;
   (f) a polyalkylene glycol in an amount from about 0.5 to about 5.0 weight percent of the total composition;
   (g) a moisturizer and/or emollient selected from the group consisting of polyols and cetylethers in an amount from about 0.05 to about 5.0 weight percent of the total composition; and
   (h) water in an amount from about 6 to about 30 weight percent of the total composition.

2. The skin disinfecting formulation of claim 1 further comprising:
   (i) a thickening agent in an amount from about 0.01 to about 3 weight percent of the total composition wherein said thickening agent is selected from the group consisting of poly(oxpropylene) poly-(oxyethylene) condensates, hydroxypyopyl methylcelluloses and carbopol polymers.

3. The skin disinfecting formulation of claim 1 further comprising:
   (i) a preservative in an amount from about 0.01 to about 5 weight percent of the total composition.

4. The skin disinfecting formulation of claim 1 wherein said alcohol is ethanol or isopropanol.

5. The skin disinfecting formulation of claim 3 wherein said preservative is parachlorometaxylenol, hexetidine or bis-biguanides.

6. The skin disinfecting formulation of claim 1 further comprising an acid to adjust the pH in the range of from about 5 to about 8.

7. The skin disinfecting formulations of claim 6 wherein said acid is hydrochloric acid, citric acid or phosphoric acid.

* * * * *